United States Patent [19]

Goodman

[11] Patent Number: 5,336,446
[45] Date of Patent: Aug. 9, 1994

[54] COMPOSITIONS AND PROCESS FOR NON-IRRITATING DENSE FOAMING OF BATH WATER AND PERI-VAGINAL CLEANING

[76] Inventor: Robert M. Goodman, 1402 Astor Ave., Bronx, N.Y. 10469

[21] Appl. No.: 922,010

[22] Filed: May 1, 1992

Related U.S. Application Data

[63] Continuation of Ser. No. 577,951, Sep. 5, 1990, abandoned, which is a continuation-in-part of Ser. No. 312,924, Feb. 21, 1989, abandoned.

[51] Int. Cl.$^5$ ............................ C11D 1/90; C11D 1/94; C11D 1/12
[52] U.S. Cl. ............................ 252/554; 252/DIG. 5; 252/DIG. 14; 252/558; 252/547
[58] Field of Search ............... 252/DIG. 5, DIG. 14, 252/547, 174.21, 554, 558

[56] References Cited

U.S. PATENT DOCUMENTS

| | | | |
|---|---|---|---|
| 3,328,307 | 6/1967 | Schmitz | 252/106 |
| 3,533,955 | 10/1970 | Pader et al. | 252/153 |
| 3,928,251 | 12/1975 | Bolich, Jr. et al. | 252/545 |
| 4,306,997 | 12/1981 | Oneto et al. | 252/541 |
| 4,426,310 | 1/1984 | Verunica | 252/106 |
| 4,554,098 | 11/1985 | Klisch et al. | 252/547 |
| 4,772,424 | 9/1988 | Greeb | 252/546 |

OTHER PUBLICATIONS

"Sulfosuccinate Surfactants," Cosmetics and Toiletries, Schoenberg, vol. 104, Nov. 1989 pp. 105–112.

"Formulating Mild Skin Cleansers" by Tom Schoenberg, published in Soap/Cosmetics/Specialties. May 1983.

"The Effect of Bubble Bath on the Urinary Tract," by Sumner, Marshal, published in Journal of Urology, vol. 93 (1965) No month available.

"Soap is the Major Cause of Dysuria", by U. Ravnskov. The Lancet, May 5, 1984.

"Shampoo Urethritis", by William B. Rogers, MD. The Pediatric Forum, vol. 139 (Aug. 1985).

"The Gynecology of Childhood and Adolescence", by John W. Huffman, MS, MD, et al., published by N. B. Saunders Co. (1981). No month available.

"Formulating Mild Foaming Bath Products," Cosmetics and Toiletries, Schoenberg, vol. 100, May 1985.

Primary Examiner—Paul Lieberman
Assistant Examiner—Michael P. Tierney

[57] ABSTRACT

A surfactant to produce in the bath a wet foam non-irritating to the urogenital areas comprising salts of anionic surfactants and N substituted betaines having aliphatic primary alkyls and/or fatty amido alkyls as the N substituents and the anionic surfactant salts are monoesters of sulfosuccinate with saturated straight chain radicals and a method to clinically test such components.

5 Claims, No Drawings

COMPOSITIONS AND PROCESS FOR NON-IRRITATING DENSE FOAMING OF BATH WATER AND PERI-VAGINAL CLEANING

This application is a continuation of Ser. No. 07/577,951, filed Sep. 5, 1990 now abandoned which is a continuation-in-part of my application Ser. No. 07/312,924, filed Feb. 21, 1989 and now abandoned.

BACKGROUND OF THE INVENTION

This invention relates to a method of testing surfactant compositions for urogenital irritancy on individuals having particular susceptibility and to compositions comprising sulfosuccinate monoesters, other anionic surfactants, and betaine surfactants which produce no irritation in the disclosed test. The compositions produce especially fine wet foam, the wetness of which precludes eye sting. It also relates to a method of producing voluminous foam on bath water having the above qualities of freedom from urogenital irritation in susceptible individuals.

Aqueous surfactant compositions have long been used in toiletries for cleaning and foaming. Children in particular enjoy playing with and in foams. Three problems are encountered thereby.

Firstly, exposure of desired duration to desired concentrations of surfactants causes an irritant urethritis and/or vulvovaginitis in susceptible individuals. See for instance S. Marshall, "The Effect of Bubble Bath on the Urinary Tract", *J. Urology* vol. 93 (1965), p. 112; U. Ravnskov, "Soap Is the Major Cause of Dysuria", *Lancet* 1984, part 1, pp. 1027-8; and W. B. Rogers, "Shampoo Urethritis", *Amer. J. of Diseases of Children*, vol. 139 (1985), pp. 748-9. Huffman et al., *The Gynecology of Childhood and Adolescence* (1981 W. B. Saunders) on page 114 observe this "allergic vulvitis" to be distinct from skin irritation: "A soap that does not affect the skin elsewhere on the child's body may, however, cause an allergic vulvitis." Accordingly, it is an object of my invention to provide a surfactant or bubble bath that does not cause such irritation in susceptible persons. It is an object to provide a useful method of testing such products.

Secondly, foams produced by common compositions on bath water soon become dry and brittle. The dryness causes eye sting when the foam contacts the cornea, and the brittleness diminishes the play value and/or the desired pleasant qualities of the foam. I have found a direct relationship between foam dryness and eye sting as hereinafter more clearly disclosed. It is thus a further object of my invent ion to produce a foam that retains its elasticity, softness and wetness.

Thirdly, voluminous persistent foams produced by currently available products leave a skin residue unpleasant to some individuals. My compositions, possibly because they form wetter foams, do not appear to have this drawback, and rinsing is reduced or eliminated.

The prior art acknowledges the desirability of compositions for peri-vaginal cleaning and the foaming of bath water without urogenital irritation. Tom Schoenberg in "Formulating Mild Foaming Bath Products", *Cosmetics & Toiletries* 100:5, May 1985, pp. 53-7 teaches this object in disclosing several compositions, but uses only skin irritancy as a test criterion. Snoopy Bath Bubbles, a discontinued product of Creative Specialties, Ltd., Jersey City, N.J. 07306, was tested for skin and urogenital irritation on a panel of 24 prepubertal girls (William Waggoner, "Bubble Bath and Bath Products" in Waggoner, ed., *Clinical Safety and Efficacy Testing*, Marcel Dekker 1989) Summer's Eve Feminine Wash, a perivaginal cleaner from C. B. Fleet Co., Lynchburg, Va. 24506, was tested on 150 normal adult women.

It is an object of my invention to provide a testing method using only individuals susceptible to urogenital irritation independently of the presence or absence of skin irritation to other areas of the body. The Snoopy and Summer's Eve tests specifically screened out subjects with a history of susceptibility to urogenital irritation from toiletries. Indeed, my desideratum for both testing and composition is contrary to this prior art teaching which did not fully appreciate the distinction between urogenital irritation (including vulvitis) and skin irritations of other body parts in general.

Eye sting is a subjective symptom reported by subjects when any of various solutions are applied to the cornea. Eye irritation is an objective sign. Ordinarily, a solution which irritates the eye will cause sting in the process. The cornea is also sensitive to increases in osmolarity, and application of a hypertonic solution, even if non-irritating, will ordinarily sting. The strategy extant in the art for countering eye sting, as in baby shampoos, has been to combine a formula low in eye irritancy with polyethoxylates of either monoglycerides or synthetic glycolipids. These nonionic surfactants counter eye sting, but may compromise other qualities of surfactant compositions.

Some prior art compositions teach combining sulfosuccinate monoesters and betaine surfactants as major ingredients, chiefly to reduce skin and eye irritation: Eugene Frank, "Formulation Technology of Liquid Soaps", *Cosmetics & Toiletries* 97, July 1982, pp. 49-54, Formula 9; Schoenberg, op. cit., and "Formulating Mild Skin Cleansers", *Soap/Cosmetics/Chemical Specialties*, May 1983, pp. 33-7 and 95; surfactant supply companies Scher, Mona and Jordan, *Cosmetics & Toiletries* 101, July 1986, pp. 86-7, formulas for Pearlescent Bubble Bath, Natural Conditioning Bubble Bath, and Mild Bubble Bath; Mona Industries Technical Bulletin #284, January 1985, Mild Baby Bubble Bath. The general idea (but no specific formula range) of such a combination, but with a different object, is also among the many suggested in the disclosure of Morton Pader, U.S. Pat. No. 3,533,955. A sulfosuccinate and betaine are relatively minor constituents of formulas disclosed by Pierre Verunica, U.S. Pat. No. 4,426,310, and may be present in some of the possible formulas in the disclosure of Klisch et al., U.S. Pat. No. 4,554,098. Such prior art fails to suggest the superiority of such agents and the need to employ them in a major role exclusive of or outweighing other aspects.

SUMMARY OF THE INVENTION

The present inventive compositions are mixtures of anionic surfactants with betaines as the sole foam stabilizers. The anionic surfactants comprise an obligatory alkyl sulfosuccinate monoester, which allows for a very fine wet foam, and variable amounts of other anionic surfactants, which increase the volume and persistence of the foam. The wetness of the draining foam can be demonstrated by its failure to produce eye sting.

The novel method of testing begins by selecting subjects with an unmistakable, reproducible history of genital and/or urinary irritation produced by exposure to surfactant-containing preparations. Subjects tested the compositions by direct perivaginal cleaning and/or an exaggerated bath exposure.

The exaggerated bath exposure is produced by having the tester sit in shallow water to which test material is added, before completing its dilution with water to full bath depth. The high concentration of material not only increases the sensitivity of the test, but also makes possible an efficient foaming method, wherein the solution is aerated by splashing before the bather sits.

DETAILED DESCRIPTION OF THE INVENTION

Compositions for Dense Foaming

The present inventive compositions comprise (1) anionic surfactant(s) and (II) amino carboxylic acid betaine surfactant(s). Preferred betaines are fatty alkyl amides of N-propylamino-N, N-dimethylammonio acetic acid.

Component I comprises (III) an obligate fatty monoester sulfosuccinate salt, and variable amounts of (IV) a fatty oligo (ethyl ether) monoester sulfosuccinate salt and/or (V) any of various monoanionic surfactants. Sulfosuccinate esters are the articles of commerce given by the product of bisulfites with maleic esters.

Compositions that have tested well include (I) salts of ionic surfactants and (II) an N-substituted, N,N-dimethyl betaine of glycine, wherein the N substituent is taken from the group consisting of a $C_{10-18}$ straight-chain saturated aliphatic primary alkyl group, or a $C_{10-18}$ fatty (or odd-carbon analog) amido short alkyl group, or mixtures thereof; wherein the anionic surfactant salts (I) are (III) a monoester of sulfo-succinate with a straight-chain saturated primary alcohol, (IV) a monoester of sulfo-succinate with a 1-6 mole ethoxylate of a straight-chain saturated primary alcohol and (V) at least one sulfonation product of the group consisting of alkyl (ethyl ether)$_{1-7}$, alkyl (ethyl ether)$_{1-7}$ alcohol, $C_{12-16}$ alkane, alpha olefin, alkyl benzene, alcohol or ester; wherein the anionic salts (I) are in the relationship $(a+2b)/(c-b)=r$, wherein a, b, and c are the mass proportions of IV, V, and III, respectively, and r is from 0 to 4.6.

Examples of such compositions are given in Table I. Formulas are given by the active mass percentage of surfactant ingredients shown. "$C_{12}SO_3$ succinate" is diammonium lauryl sulfosuccinate monoester. "$C_{12}(Oet)_3SO_4$" is sodium lauryl (ethyl ether)$_3$ sulfate. The amidopropyl (dimethyl) betaines (of glycine) are of lauric ("$C_{12}$"), myristic ("$C_{14}$"), palmitic ("$C_{16}$"), and coconut ("$C_{10-18}$") acids. "$C_{12}(etOH)_2$amide" is lauric diethanolamide. The fatty moieties are heterodisperse in these commercial ingredients. A 35% active concentrate of Example 1 is conveniently prepared by mixing 40% diammonium lauryl sulfosuccinate, 30% lauramidopropyl dimethyl glycine betaine, and 28% sodium lauryl (ethyl ether)$_3$ sulfate in an 8:5:3 volume ratio.

Foaming properties were tested in a cylinder shake system. A polycarbonate cylinder of 11.2 cm internal diameter was charged with New York City tap water (6 ppm $Ca^{++}$ and 6ppm $Mg^{++}$) at 30°–32° C. and test concentrate to a total volume of 500 ml, leaving 18 cm head space under the lid. The cylinder was then quickly shaken vertically ten times, and placed in a bath of 30°–32° C. At times indicated in Table I, the height of foam was determined as the mean of the highest and lowest top bubble film above the solution; "*" means the lid produced an artifact.

TABLE I

| | Example | | | | | | | | |
|---|---|---|---|---|---|---|---|---|---|
| | 1 | 2 | 3 | 4 | 5 | 6 | 7 | 8 | 9 |
| | mass % of total surfactant compo | | | | | | | | |
| $C_{12}SO_3$ succinate | 58 | 73 | 43 | 67 | 45 | 58 | 58 | 58 | 58 |
| $C_{12}(Oet)_3 SO_4$ | 15 |  | 30 | 17 | 12 | 15 | 15 | 15 | 15 |
| amido-propyl betaine | | | | | | | | | |
| $C_{12}$ | 27 | 27 | 27 | 16 | 43 | | | | 18 |
| $C_{14}$ | | | | | | 27 | | | |
| $C_{16}$ | | | | | | | 27 | | |
| $C_{10-18}$ | | | | | | | | 27 | |
| $C_{12}(etOH)_2$ amide | | | | | | | | | 9 |

| | | | total active w/v | | | | | | | | | | | | | | | | | | | | | | | | |
|---|---|---|---|---|---|---|---|---|---|---|---|---|---|---|---|---|---|---|---|---|---|---|---|---|---|---|---|
| | Ex 1 | | | Ex 2 | | | Ex 3 | | | Ex 4 | | | Ex 5 | | | Ex 6 | | | Ex 7 | | | Ex 8 | | | Ex 9 | | |
| minutes | height, mm | fine-ness | eye sting | height, mm | fine-ness | eye sting | height, mm | fine-ness | eye sting | height, mm | fine-ness | eye sting | height, mm | fine-ness | eye sting | height, mm | fine-ness | eye sting | height, mm | fine-ness | eye sting | height, mm | fine-ness | eye sting | height, mm | fine-ness | eye sting |
| $2 \times 10^{-4}$ | | | | | | | | | | | | | | | | | | | | | | | | | | | |
| 1 | 68 | 5 | 0 | 67 | 5 | 0 | 101 | 3 | 0 | 66 | 5 | 0 | 65 | 5 | 0 | 69 | 5 | | 55 | 7 | 0 | 64 | 5 | | 70 | 6 | 0 |
| 5 | 62 | 6 | 0 | 45 | 9 | 0 | 98 | 1 | 0 | 65 | 6 | 0 | 58 | 7 | 0 | 56 | 7 | | 51 | 8 | | 64 | 5 | | 70 | 6 | 0 |
| 15 | 47 | 7 | 0 | 35 | 9 | 0 | 98 | 1 | 0 | 42 | 9 | 0 | 55 | 5 | 0 | 48 | 7 | | 44 | 9 | | 47 | 7 | 2 | 70 | 6 | 1 |
| 30 | 40 | 8 | 1 | 29 | 10 | 0 | 97 | 0 | 2 | 41 | 8 | 0 | 49 | 4 | 2 | 47 | 7 | 1 | 40 | 9 | 0 | 47 | 6 | | 54 | 6 | 3 |
| $4 \times 10^{-4}$ | | | | | | | | | | | | | | | | | | | | | | | | | | | |
| 1 | 94 | 5 | 0 | 82 | 5 | 0 | * | 5 | 0 | 106 | 5 | 0 | * | 3 | 0 | 73 | 6 | 0 | 80 | 5 | 0 | 97 | 3 | | * | 3 | 0 |
| 5 | 85 | 4 | 0 | 62 | 9 | 0 | | 4 | 2 | 106 | 5 | | | 3 | 2 | 68 | 7 | 0 | 62 | 7 | 0 | 92 | 6 | | | 5 | 1 |
| 15 | 74 | 5 | 2 | 53 | 10 | 2 | | 3 | 2 | 75 | 7 | | | 3 | 2 | 68 | 7 | 2 | 55 | 8 | 1 | 88 | 6 | 1 | | 8 | 3 |
| 30 | 68 | 5 | 2 | 47 | 9 | 2 | | 5 | 3 | 67 | 7 | 0 | | 2 | 3 | 68 | 4 | 3 | 51 | 8 | 3 | 86 | 5 | | | 7 | 3 |

Bubble size was noted near the top and bottom of the column of foam. Foam fineness is a nonlinear subjective score based on this observation, scaled from 0 for the largest to 10 for the smallest bubbles.

Eye sting determinations were conducted separately. The top 2 cm or so of foam was spoon sampled, and touched to both eyes. "0" means no sensation, or sensation in only one eye. "1" means slight sensation in both eyes. "2" means definite pain in one eye. "3" means definite pain in both eyes. Between eye sting samplings, and throughout foam experiments, the cylinder was undisturbed in the bath with the lid on.

In any solution with film-forming properties, foam forms when bubbles reach the surface. At first the bubbles are spherical, trapping liquid in the interstices where the curvature of the bubbles permits little more than point contact, producing a wet foam. Bubbles lubricated by the interstitial liquid slip past each other easily, so wet foam is very plastic. The interstitial liquid makes the spherical-stage foam heavy. The weight and plasticity combine to make a runny, liquid-like phase lying flat atop the solution.

Foam matures by draining from top to bottom into the bulk solution. First the interstices drain, causing the bubbles to form larger interfaces of films. When most of the interstitial solution has drained, the bubbles are polyhedral. Although polyhedral foam is known as dry foam, its films can still have a variable amount of liquid, corresponding to their thickness. The films continue to drain and become thinner until a limit is reached such that further drainage must break the bubbles. That limit depends on the solution in question, as does the tendency of the bubbles to persist at that limit.

Wet foam is opaque, becoming more transparent as it dries. If liquid is percolated through a transparent, dry foam from above, the foam regains its whiteness.

A drying foam also loses weight, and changes rheologic properties. First its plasticity decreases, as there is less liquid in which the bubbles can flow past each other. Together with the loss in mass, this produces a less runny foam. However, the bubbles are still able to deform without breaking, so the foam is still fairly plastic, with some elastic recoil. A mass of such foam tends to hold a shape. As its limit of dryness is approached, the foam becomes very light and brittle—unable to deform without collapsing.

As foam dries, its interface to volume ratio increases. Because surfactants concentrate at surfaces, the concentration of surfactant must therefore increase. I have discovered that, once a foam dries to a certain degree, its osmolarity reaches the point that it is sensible, then painful, when touched to the eye. The utility of a composition which makes a foam which remains wet enough not to cause this problem is manifest, especially when children's evaluations are taken. The nonionic surfactants used to counteract eye sting in baby shampoos are expensive and tend to compromise foam qualities, and their use is obviated by the present invention.

Density of foam is a product of its wetness and fineness. Although the size of an isolated bubble is a function of its internal pressure and surface tension, that relationship does not predict the distribution of bubble sizes in a foam, which changes as bubbles of various sizes break or coalesce.

Formulators of bubble bath preparations have concentrated on maximizing volume and persistence in a static test of foam from a given concentration of active matter—usually producing a dry, lacey foam of large bubbles. I observe that many users of such products, especially children, prefer denser foam. Under play conditions, fine wet foam, as produced by Examples 1, 2 and 7, is often reported as more persistent than that of formulas which are far superior in volume and persistence in static tests.

Testers did blind comparison baths or water play tests with Example 1 versus one of the following: Ivory Dishwashing Liquid (or a surfactant replica prepared according to the preferred embodiment of Donald Bissett, U.S. Pat. No. 4,555,360), Snoopy Bath Bubbles (whose label discloses lauramidopropyl betaine, sodium lauryl sulfate, ammonium lauryl sulfosuccinate, lauramide DEA, and polysorbate 20), 6:1 mass ratio sodium lauryl (ethyl ether)$_3$ sulfate with lauric diethanolamide, another hand dish detergent, and other bubble baths. The difference in foam quality was noted by all, and the denser foam of the present invention was preferred except insofar as it obscured water toys.

Many monoanionic surfactants common to the art—sodium lauryl sulfate, sodium $C_{14-16}$ alpha olefin sulfonate, sodium dodecylbenzene sulfonate, sodium lauryl sulfoacetate, and sodium lauryl methyl ester sulfonate—behave about the same as the alkyl ether sulfate in this system, in that replacement of a portion of the alkyl sulfosuccinate by them progressively increases the volume and persistence, at some sacrifice in density, of the foam produced. Sodium branched tridecyl (ethyl ether)$_3$ sulfate was markedly inferior in this role, while sodium N-lauroyl sarcosinate was absolutely ineffective.

Other dianionic surfactants fail to substitute for lauryl sulfosuccinate. With disodium oleamidoethyl sulfosuccinate, and even more so with disodium decyl (ethyl ether)$_6$ sulfosuccinate, the foam was drier and less fine, with monosodium N-cocoyl glutamate, the foam was fairly fine, but dry (as felt by eye sting) and less persistent, whether or not the component was titrated to dibasic.

Lauryl oligo (ethyl ether) sulfosuccinates behave somewhat between lauryl sulfosuccinate and monoanionics in this system; the greater the ethoxylation, the more like the monoanionic. Disodium lauryl (ethyl ether)$_3$ sulfosuccinate acts approximately like a 1:1 mass mixture of lauryl sulfosuccinate and lauryl ether sulfate in this system. However, ethoxylation of alkyl sulfate in the 0–3 mole range as the monoanionic surfactant in this system has no significant effect on foam qualities.

These findings are expressed in the relation $r=(a+2b)/(c-b)$, where a, b and c are the respective mass proportions of lauryl ether(3) sulfosuccinate, monoanionic surfactant, and lauryl sulfosuccinate, respectively. As r increases, so does the volume and persistence of the foam. The fineness and wetness of the foam is maximal when $r=0$. In Examples 1 and 6–9, $r=0.7$.

As Klisch et al. (U.S. Pat. No. 4,554,098) teaches, the foam can be stabilized further by partly replacing the betaine with an alkanolamide surfactant. It is not clear whether formulas such as those of Snoopy Bath Bubbles are pursuing that strategy, or whether they incorporate such ingredients mainly to thicken the concentrate. However, nonionic foam stabilizers are detrimental to the advantageous foaming qualities and other properties of the present invention. See Example 9. Alkanolamide and amine oxide foam stabilizers promote foams of very thin films, which are very dry. They act as if they had a high "r" value in the above relation. Alkanolamides also waterlog skin faster. Such thickeners also impair rapid dilution of a concentrate in bath water.

However, foams don't have to have any stabilizers to be dry enough to sting eyes. For instance, the settled foam of Sesame Street liquid bubble bath, whose surfactant ingredients are disodium lauryl (ethyl ether)$_3$ sulfosuccinate and sodium lauryl oligo(ethyl ether) sulfate, stings eyes as sharply as when supplemented with lauric diethanolamide.

Higher r values (up to 4.6) in this system, or common compositions producing fluffier and more persistent foam, are also associated with a more slippery feeling of the water during use, and a stickier feeling during and after use.

The present invention relies on use in water of some hardness for full density of foam. The effect of soft water is to produce results corresponding to a higher than actual r value.

Prior art compositions superficially similar to the present invention have noticeably different foam properties. Mona's "Mild Baby Bubble Bath" (diammonium lauryl sulfosuccinate 45%, lauramidopropyl betaine 28%, and lauroamphocarboxyglycinate 27%) is claimed to produce "large and voluminous bubbles", not fine foam. "Natural Conditioning Bubble Bath", similar but with an alkanolamide, should be similar. When 2-cocyl-3-hydroxyethyl-1-imidazoliumyl propionate (cocamphopropionate) is substituted for the lauroamphocarboxyglycinate in "Mild Baby Bubble Bath", a large-bubble foam also results. Substituting cocamphopropionate for the betaine in Examples 1 and 2 of the present invention produced foam inferior in both density and persistence.

Though Schmitz (U.S. Pat. No. 3,328,307) teaches "dense and stable foam of superior quality" using betaine surfactants alone, single betaines and mixtures of betaines disclosed therein or commonly used in the art make a much drier foam by themselves than the present invention. The choice of betaine in the present inventive system is also important. Isostearamidopropyl dimethyl betaine, when used instead of the alkamidopropyl betaines of the Examples, made a much less persistent foam, while oleyl dimethyl betaine in that role made foam inferior in both volume and persistence.

The exact proportion of anionic surfactants to betaines is not critical. However, a mass ratio of 2.7: 1 is optimal. Raising the ratio above 6:1 diminishes the foam's persistence unacceptably, while lowering it below 1:1 makes the foam too dry. Among the fatty amidopropyl dimethyl glycine betaines in this styem, lauric is best for rapid development of wet foam, while palmitic makes the finest foam, with excellent persistence. Mixtures of commercial lauric and palmitic amidopropyl betaine perform better all around than do cocamidopropyl and myristamidopropyl betaines.

Within the range specified by Frank (op. cit), the following analog of Example 1 was prepared: disodium oleamidosulfosuccinate 58%, cocamidopropyl betaine 27%, and sodium N-lauroyl sarcosinate 15%. This produced very voluminous and stable foam, but it was quite dry and stung eyes sharply. This is surprising in view of the fact that acyl sarcosinate, used alone, produces a much finer, wetter foam than the sulfate/sulfonate monoanionics it substituted for therein. The choice of sulfosuccinate monoester is evidently critical in producing the desired foam qualities.

TESTING AGAINST UROGENITAL IRRITATION

Test subjects were selected by medical history of reproducible symptoms in relationship to relevant exposures. Qualifying conditions were vulvitis, vaginitis, and urethritis, manifested as episodes of infrapubic pain, dysuria, or urinary frequency. Symptoms must have occurred within hours after exposure, and lasted for more than an hour, but not more than three days. An exposure was usually one bath or washing of the external genitalia; however, where irritation is subclinical after one such exposure, but lasts long enough to become symptomatic after exacerbation by similar exposures within a given day or on subsequent days, that set of exposures can be considered one exposure. Infection, atopic reaction, and general dermatitis must have been ruled out as causing the symptoms.

Materials qualifying as causing relevant exposures included any of a variety of surfactant-containing preparations. These could include toilet soap, shampoo, bubble bath, shaving cream, household detergent, play foam, bath oil with emulsifier, baby bath, shower gel, and spermicide. Where exposure of similar magnitude of a person's genitals to preparations led to irritation in the case of one surfactant preparation, but a closely similar surfactant composition was well tolerated, the reaction was assumed to be atopic, not irritant. This would be the case where someone reacted differently to differently perfumed versions of a soap, for example. However, where someone tolerated soaps (e.g. , those from Armour) with a low content of short-chain fatty acids, but reacted to soaps with a relatively high short-chain content (e.g. , Camay, Coast, Ivory), the difference was laid to surfactant irritancy.

Reproducibility was judged by the following criteria: (1) More than one episode must have been experienced, clearly separated by an asymptomatic period. (2) Following recognition of the syndrome, every subsequent exposure to the same, or a closely similar, composition must have led to similar symptoms, unless the magnitude (measured by concentration of surfactant, and duration, and sometimes frequency, of exposure) was below a threshold established by that person's history. (3) The time between the last episode and the present test must have been small compared to the duration over which the syndrome was noticed in the person, and puberty must not have intervened between the last episode and the present test. Surfactant urogenital irritancy is believed to decline at puberty, although I have found instances of its occurring after puberty with no adverse experience despite exposure prior to puberty.

Subjects selected by these criteria did one or both of two tests on surfactant compositions. In one test, a 35% active test solution was used as a perivaginal and female perineal cleaner, in the manner of soap, followed by rinsing as usual. The other test was to add log active test material to approximately one inch depth bath water, splash the water to mix and foam by aeration, then have the tester sit in this solution of high concentration before running in water to usual bath depth. Where the magnitude of exposure necessary to reproducibly elicit symptoms according to the subject's history included a certain frequency of use, that frequency was exceeded for the test.

Extant foaming bath preparations recommend, to lessen irritation, running in water to its final dilution before entering the water. However, the dry body passing through the foam breaks much of it. Attempts to regenerate the foam by splashing fail because the surfactant is too dilute. As a method of use, the present inventive test method avoids this problem, providing the composition passes the test against urogenital irritancy.

The following compositions caused no symptoms in these tests of urogenital irritancy:

TABLE II

| Example from Table I | 1 | 2 | 7 | 8 | 10 | 11 | 12 |
|---|---|---|---|---|---|---|---|
| mass percentage/ | | | | | | | |
| $(NH_4)_2$lauryl $SO_3$suc'ate | 58 | 73 | 58 | 58 | 43 | 43 | 65 |
| $Na_2$laur(eth)$_3SO_3$suc'ate | 0 | 0 | 0 | 0 | 30 | 30 | 0 |
| Na lauryl(ether)$_3$sulfate | 15 | 0 | 15 | 15 | 0 | 0 | 8 |
| lauramidopropyl betaine | 27 | 27 | 0 | 0 | 27 | 0 | 18 |
| palmitamidopropyl betaine | 0 | 0 | 27 | 0 | 0 | 27 | 9 |
| cocamidopropyl betaine | 0 | 0 | 0 | 27 | 0 | 0 | 0 |

I found that I can get foaming with concentrations of my material as low as two parts per million. However, to test for genital irritation, I have used as high as four hundred parts per million as follows. 20 grams of material is placed in 50 liters of water. Foam is generated by splashing and aerating and the subject seated in the foamed material, the bath is then diluted about five times to 250 liters of water or 80 parts per million. Since the initial transient concentration of 400 parts per million far exceeds amounts usually employed for bubble bath, the test if negative is even more clinically convincing. Tests, of course, as in perivaginal cleaning, may also be conducted using higher concentrations of active ingredient ranging from 35% to 95%.

I claim as my invention:

1. A composition comprising (I) anionic surfactant salts and (II) an N-substituted, N,N-dimethyl betaine of glycine, wherein the N substituent is selected from the group consisting of a $C_{10-18}$ straight-chain saturated aliphatic primary alkyl group, or a $C_{10-18}$ fatty amido alkyl group, or mixtures thereof; wherein the mass ratio of I to II is from 1:1 to 6:1; wherein the anionic surfactant salts (I) are selected from the group consisting of (III) a monoester of alkali metal lauryl sulfosuccinate with a straight-chain saturated primary alcohol, (IV) a monoester of sulfosuccinate with a 1–6 mole ethoxylate of a straight-chain saturated primary alcohol, and (V) a sulfonation product, wherein the compound to be sulfonated is selected from the group consisting of $C_{10-18}$ alkyl (ethyl ether)$_{1-7}$, alkyl (ethyl ether)$_{1-7}$ alcohol, alkane, olefin, alkyl benzene, alcohol, and alkyl ester; wherein the anionic surfactants of (I) are in the relationship $(a+2b)/(c-b)=r$, wherein a, b, and c are the mass proportions of IV, V, and III, respectively, and r is from 0 to 4.6 wherein at least about 59% by weight of the anionic surfactant is (III).

2. A composition according to claim 1 wherein III is diammonium or disodium lauryl sulfosuccinate, II is lauramidopropyl dimethyl glycine betaine, V is the sodium salt of the sulfonation product of lauryl (ethyl ether)$_3$ alcohol, the mass ratio of I to II is approximately 2.7:1, a is 0, and r is from 0 to 0.7.

3. A composition in accordance with claim 1 wherein III is diammonium or disodium lauryl sulfosuccinate, II is palmitamidopropyl dimethyl glycine betaine, V is the sodium salt of the sulfonation product of lauryl (ethyl ether)$_3$ alcohol, the mass ratio of I to II is approximately 2.7: 1, a is 0, and r is from 0 to 0.7.

4. Compositions according to claim 1 wherein III is diammonium or disodium lauryl sulfosuccinate, II is lauramidopropyl dimethyl glycine betaine, IV is disodium lauryl (ethyl ether)$_3$ sulfosuccinate, the mass ratio of I to II is approximately 2.7:1, b is 0, and r is from 0 to 0.7.

5. Compositions according to claim 1 wherein III is diammonium or disodium lauryl sulfosuccinate, II is palmitamidopropyl dimethyl glycine betaine, IV is disodium lauryl (ethyl ether)$_3$ sulfosuccinate, the mass ratio of I to II is approximately 2.7: 1, b is 0, and r is from 0 to 0.7.

* * * * *